United States Patent
Wang et al.

(10) Patent No.: US 11,524,453 B2
(45) Date of Patent: Dec. 13, 2022

(54) METHODS AND SYSTEMS FOR MANUFACTURING COMPOSITE RADIATION SHIELDING PARTS

(71) Applicant: GE Precision Healthcare LLC, Milwaukee, WI (US)

(72) Inventors: Yanju Wang, Hartland, WI (US); Jimmie Autrey Beacham, West Allis, WI (US); Chad Allan Smith, Franklin, WI (US); Paul Michael Wervey, Mukwonago, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 432 days.

(21) Appl. No.: 16/708,868

(22) Filed: Dec. 10, 2019

(65) Prior Publication Data

US 2021/0170681 A1    Jun. 10, 2021

(51) Int. Cl.
| | |
|---|---|
| *B29C 64/165* | (2017.01) |
| *B33Y 70/10* | (2020.01) |
| *B33Y 10/00* | (2015.01) |
| *B29C 64/364* | (2017.01) |
| *B33Y 40/00* | (2020.01) |
| *B29K 505/08* | (2006.01) |

(52) U.S. Cl.
CPC .......... *B29C 64/165* (2017.08); *B29C 64/364* (2017.08); *B33Y 10/00* (2014.12); *B33Y 40/00* (2014.12); *B33Y 70/10* (2020.01); *B29K 2505/08* (2013.01)

(58) Field of Classification Search
None
See application file for complete search history.

(56) References Cited

U.S. PATENT DOCUMENTS

| | | | | |
|---|---|---|---|---|
| 6,776,219 | B1 * | 8/2004 | Cornie | B22D 19/14 164/516 |
| 9,790,744 | B2 * | 10/2017 | Atkins | B29C 64/165 |
| 2003/0168637 | A1 * | 9/2003 | McCord | G21F 1/106 252/500 |
| 2013/0177131 | A1 * | 7/2013 | Teng | G21K 1/02 378/4 |
| 2019/0108923 | A1 * | 4/2019 | Anderson | G21G 4/02 |
| 2019/0111480 | A1 * | 4/2019 | Barbati | B22F 12/55 |

\* cited by examiner

*Primary Examiner* — Kelly M Gambetta
*Assistant Examiner* — Andrés E. Behrens, Jr.
(74) *Attorney, Agent, or Firm* — McCoy Russell LLP (57) ABSTRACT

Various methods and systems are provided for manufacturing a radiation shielding component of an imaging apparatus. In one embodiment, the radiation shielding component may be manufactured by infiltrating metal particles with a binder solution and then curing the binder solution impregnated with the metal particles. In another embodiment, the radiation shielding component may be printed with metal powder, infiltrated with a binding agent, and then cured to polymerize the binding agent.

14 Claims, 6 Drawing Sheets

METHODS AND SYSTEMS FOR MANUFACTURING COMPOSITE RADIATION SHIELDING PARTS

FIELD

Embodiments of the subject matter disclosed herein relate to methods for manufacturing a radiation shielding component of an imaging apparatus.

BACKGROUND

Noninvasive imaging modalities may transmit energy in the form of x-ray radiation into an imaging subject. Based on the transmitted energy, images may be subsequently generated indicative of the structural or functional information internal to the imaging subject. In a computed tomography (CT) imaging system, an x-ray source generates s beam of x-ray radiation that is transmitted from the x-ray source through a collimator and the imaging subject to an x-ray detector.

The x-ray source typically comprises an x-ray tube including a cathode and an anode electrically connected to a high-voltage electrical circuit. Upon energization of the electrical circuit, which produces a potential difference of, for example, 60 kV to 140 kV, electrons are directed from the cathode to the anode. The electrons strike the anode (target) and produce high-frequency electromagnetic waves, such as x-rays, and residual thermal energy. The residual energy is absorbed by the components within x-ray tube as heat. Since the x-rays are generated in all directions, the cathode and the anode may be enclosed in a radiation shield in order to absorb scattered x-ray radiation and to direct the x-rays in a specific direction, such as towards the imaging subject.

Upon generation of the x-ray beam in the x-ray tube, the x-ray beam is collimated by passing the x-ray beam through a collimator having at least two collimator blades. Once collimated to a desired x-ray beam size, the x-ray beam exits the collimator through a specific port. A part of the x-ray beam may be reflected from the collimator blades and is absorbed at a radiation shield enclosing the collimator. The radiation shield enclosing the x-ray tube and the collimator may be made of heavy metals such as tungsten or another heavy metal. A reliable process is employed to manufacture such radiation shields using heavy metals which typically have a high melting point and high hardness.

BRIEF DESCRIPTION

In one embodiment, a manufacturing method comprises: forming a radiation shielding component including printing the component with metal powder, infiltrating the component with a binding agent, and curing the component to polymerize the binding agent.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
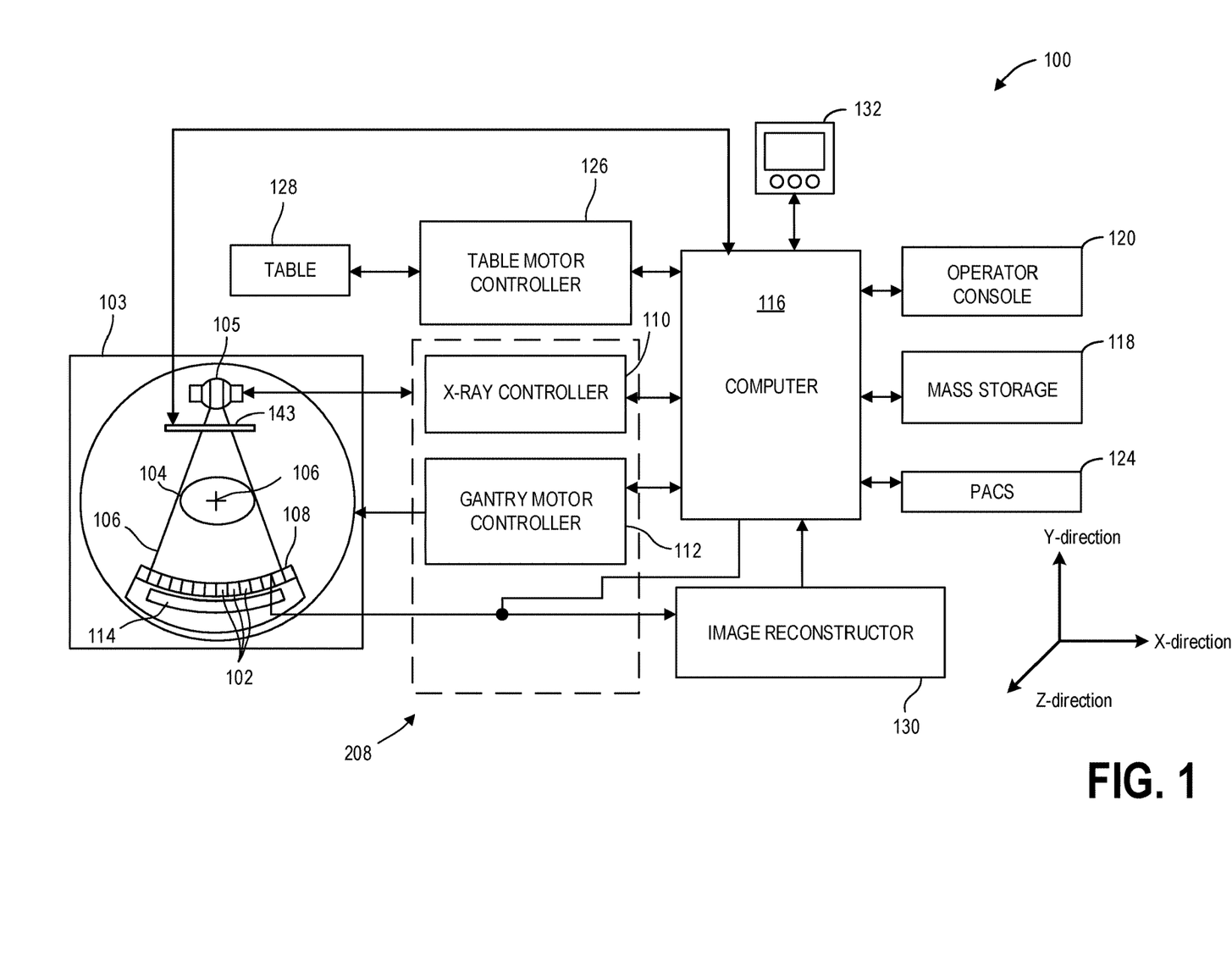
FIG. 1 shows a block schematic diagram of an exemplary imaging system according to an embodiment.
Figure 2:
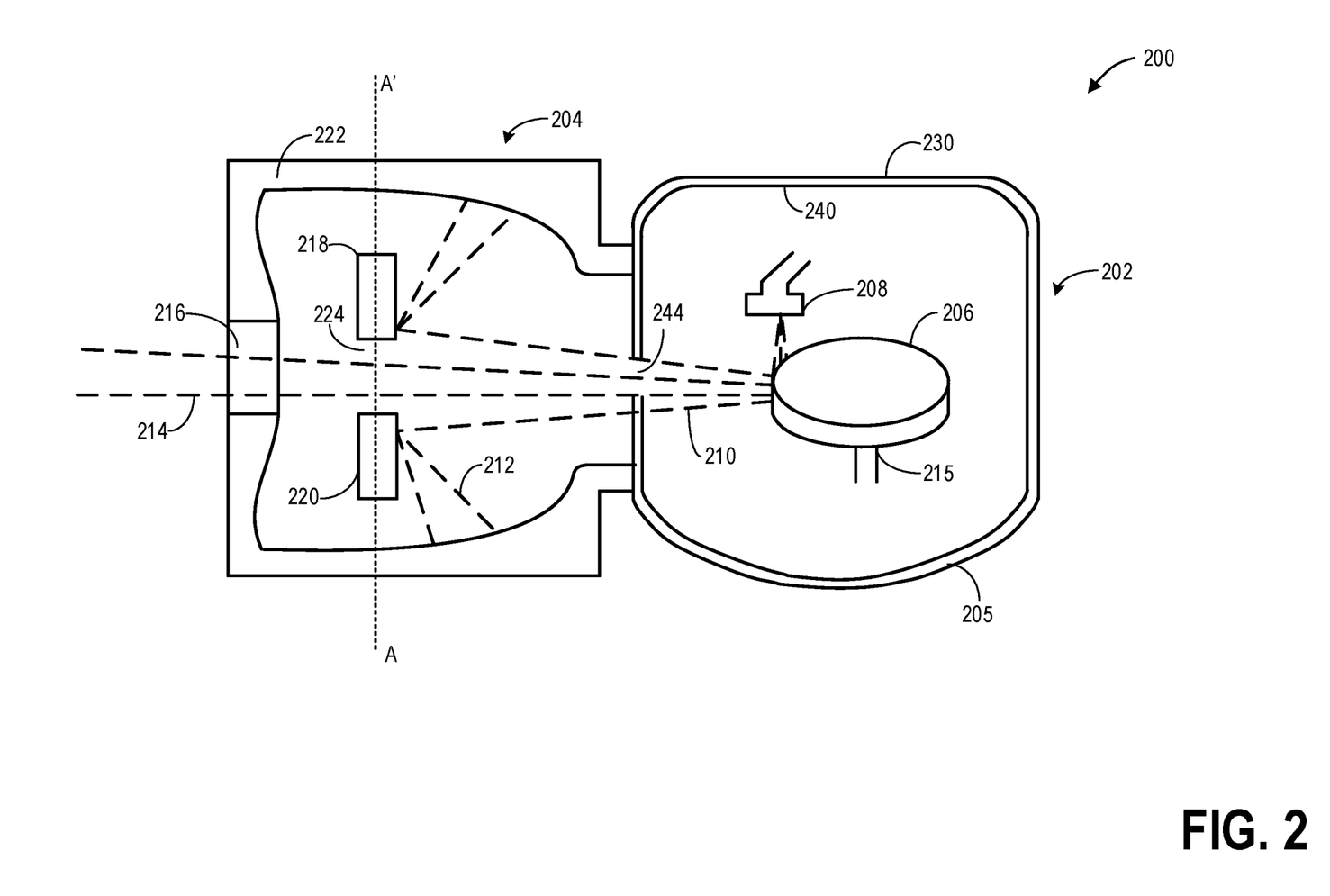
FIG. 2 shows a schematic diagram of a radiation source used in the imaging system.
Figure 5:
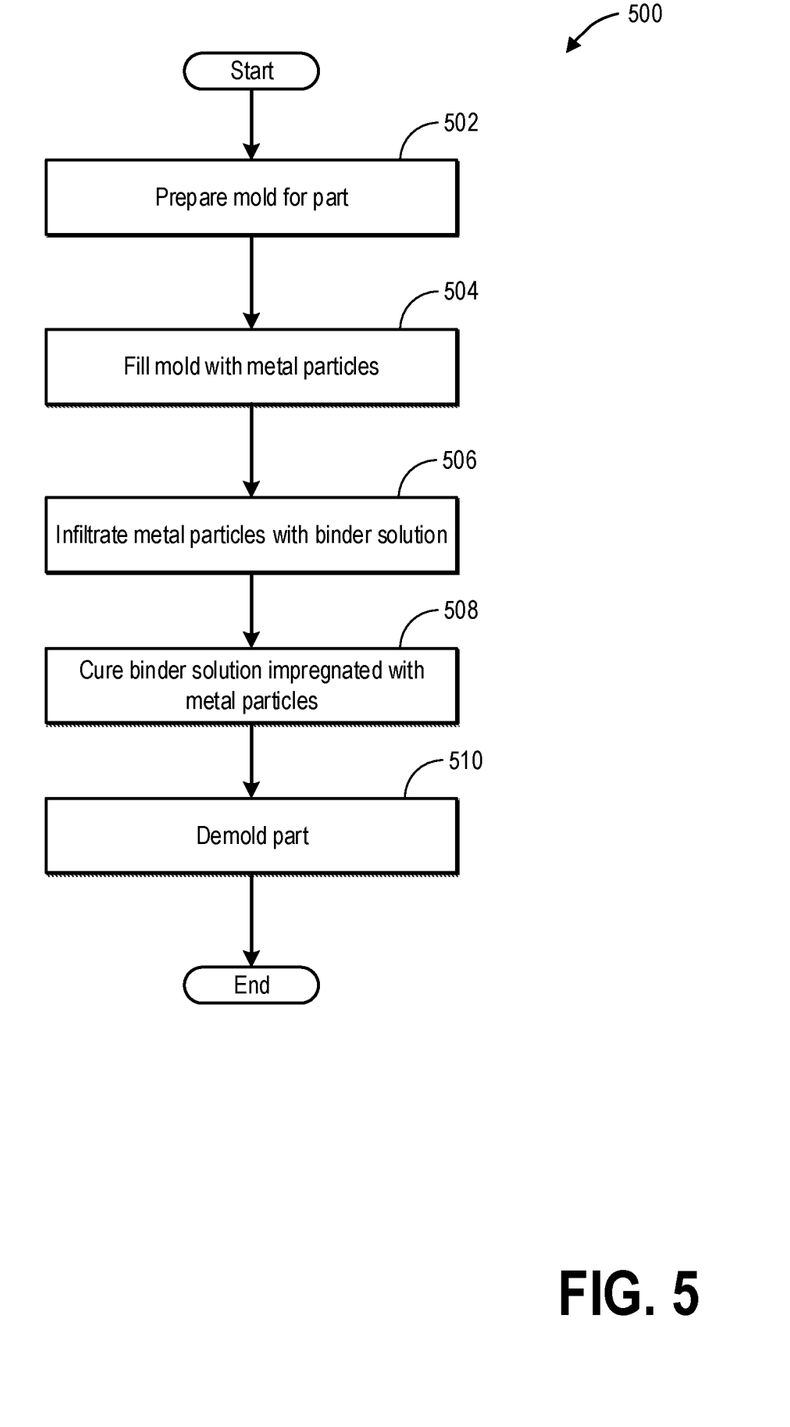
FIG. 5 shows a flow chart of an example method for manufacturing the radiation shielding component via the binder reactive injection molding process.
Figure 6:
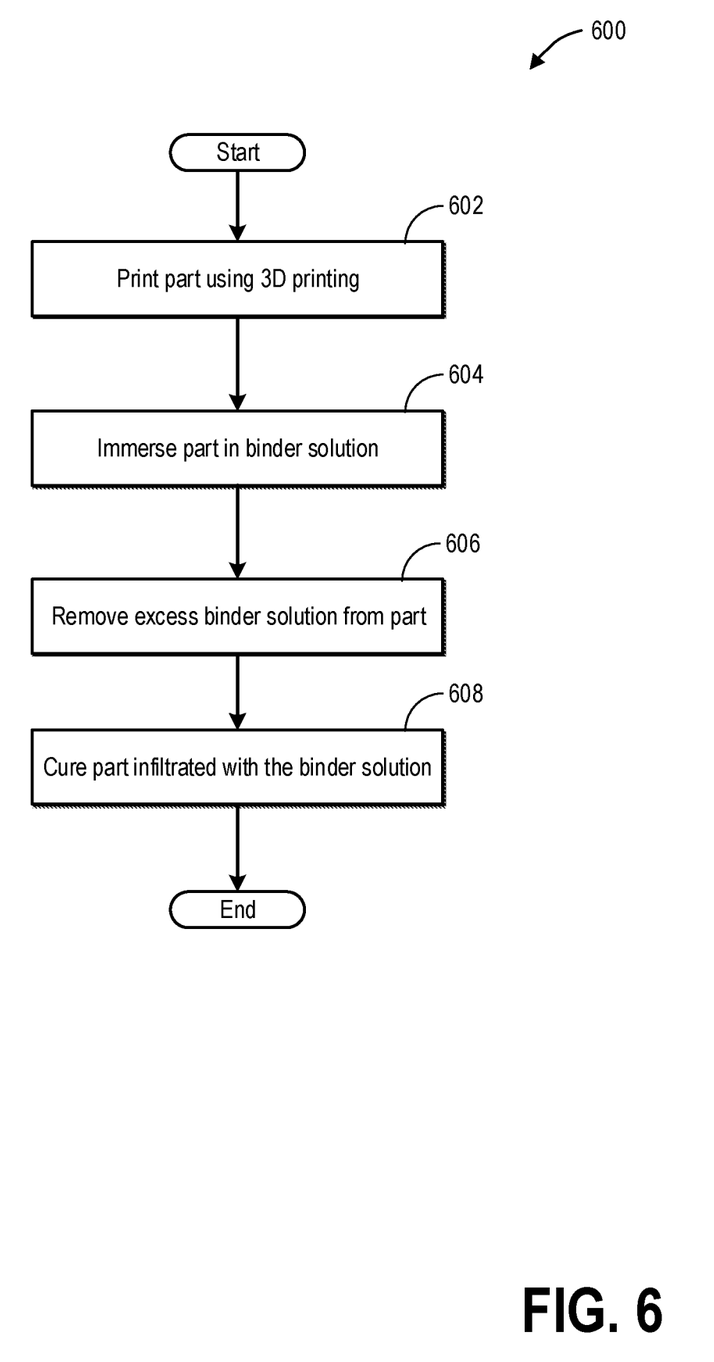
FIG. 6 shows a flow chart of an example method for manufacturing the radiation shielding component via the binder jetting and infiltration process.

The following description relates to various embodiments of radiation shielding manufacturing for an imaging apparatus. In particular, systems and methods are provided for methods for manufacturing a radiation shielding component of an imaging apparatus. FIG. 1 shows an example embodiment of an imaging system, wherein radiation shielding is included within an x-ray source. An x-ray source including an x-ray tube and a collimator at least partly enclosed within a radiation shielding is shown in FIG. 2. The radiation shielding component of the x-ray source may be made of tungsten or other heavy metal. FIG. 5 shows an example method for manufacturing the radiation shielding component included in the x-ray source via a binder reactive injection molding process. In this process, tungsten particles along with a binder is cured in a mold to produce a part having dimensions of the mold. A series of steps used in the manufacturing process of the radiation shield via the binder reactive injection molding process is shown in FIGS. 3A-3D. FIG. 6 shows an example method for manufacturing the radiation shielding included in the x-ray source via a binder jetting and infiltration process. In this process, the radiation shielding component may be manufactured by a 3D printing process followed by infiltration and subsequent curing of a binder solution in the printed radiation shielding component. A series of steps used in the manufacturing process of the radiation shield or radiation shielding component via the binder jetting and infiltration process is shown in FIGS. 4A-4D.

Though a CT imaging system is described by way of example, it should be understood that the present techniques may also be useful for manufacturing components in other x-ray imaging systems, such as x-ray tomosynthesis imaging systems, mammography imaging systems, C-arm imaging systems, interventional imaging systems, radiography imaging systems, fluoroscopy imaging systems, and so forth. The present discussion of a CT apparatus is provided merely as an example of one suitable imaging technique using radiation shields manufactured via mentioned methods.

Heavy metals such as tungsten is used for manufacturing a radiation shield included in an x-ray tube and collimator of a radiation source used in a CT system. Attributed to its higher density, non-toxic, pollution-free property of tungsten, tungsten alloy and composites have become a popular material used in the shielding applications for x-ray and gamma radiation shielding.

However, due to hardness and high melting point, it is difficult and cost ineffective to manufacture tungsten parts through traditional machining and molding. Machining may require harder and wear resistant tools for machining tungsten. Molding requires the mold to survive the melting temperature of tungsten, 3422° C. Very few materials are capable of withstanding such high temperature.

One example approach to manufacture tungsten parts include using Electrical Discharge Machining (EDM) tungsten metal directly or mixing tungsten or tungsten precursors with thermal plastics and then injection molding the part. However, screws or adhesive are required for assembling such parts in the x-ray. Also, inclusion of non-heavy metal screws in shielding parts may compromise on the shielding properties of the part. Further, traditional machining add complexity to the parts and may incur functional defects due to multistep machining assembling. Also, machining tungsten can be limiting in terms of design flexibility. As an example, the radiation shield may not be desired to be of uniform thickness, however, machining of the tungsten sheet may not provide the flexibility to vary thickness in parts, thereby leading to manufacturing of thicker, heavier parts than desired.

Based on complexity of the shielding part to be manufactured, one of two infiltration casting methods may be employed. In a first method, metal particles may be used to fill a mold and then infiltrated with a binder solution. The metal particle-solution may then be cured to form the part which may be demolded and used in the x-ray setup. The mold casting process may be cost effective and faster while providing a wider variety of binder solution options relative to options available for commercial printing and machining techniques. This process may eliminate expensive tooling, furnace usage, and high energy consumption.

In a second method, a complex shielding part may be manufactured via binder jetting and then the part may be infiltrated with a precursor and hardener/cross linker/catalyst to form the final part. Conventionally, parts manufactured directly from binder jetting printing may lack mechanical strength to be used directly in an x-ray setup. Most binders used for binding jetting printing are mixed with water, solvents, or mixture of solvents and water to enable low viscosity for smooth and stable jetting, therefore, the manufactured part may remain porous after printing and there may not be enough bonding strength to be handled directly. In addition, choices for commercial binders are limited due to their compatibility with 3D binder jetting machines. As an example, the tungsten parts prepared solely by binder jetting printing may not be used directly without infiltration of copper which is a high temperature (such as 2000° F.) and cost ineffective process. Therefore, by carrying out a post-infiltration with polymeric binders, strength of the part may be increased and the part may be directly used for radiation shielding applications. In this post-infiltration process, no high temperature processing is needed, thereby lowering the possibility of the part degrading due to the thermal mismatching and binder vaporization such as during infiltration of copper.

In this way, by using an infiltration casting method, a tungsten part may be manufactured as a single component instead of many pieces to avoid assembling. The single component without holes, joints, and connections reduces the possibility of radiation escaping the shield. The technical effect of the infiltration casting method is that the additive process provides flexibility in terms of part design, for examples, the thickness of the parts at different locations may be varied which would have been difficult through traditional manufacture as the tungsten sheets have fixed thickness. Further, the low temperature processing of the parts reduces energy consumption, during manufacturing. By using a post-infiltration process for binder jetting printed parts, strength of the parts may be improved, and the printed part may be used directly without the need for high temperature copper infiltration. Overall, by effectively manufacturing radiation shielding parts using tungsten, lead components used as radiation shields may be easier replaced.

FIG. 1 illustrates an exemplary imaging system 100 such as a CT system. In accordance with aspects of the present disclosure, the system 100 is configured to perform automatic exposure control responsive to user input. In one embodiment, the system 100 includes the detector array 108 (see FIG. 1). The detector array 108 further includes a plurality of detector elements 102 that together sense the x-ray beam 106 that pass through a subject 104 such as a patient to acquire corresponding projection data. Accordingly, in one embodiment, the detector array 108 is fabricated in a multi-slice configuration including the plurality of rows of cells or detector elements 102. In such a configuration, one or more additional rows of the detector elements 102 are arranged in a parallel configuration for acquiring the projection data.

The x-ray beam may be generated at x-ray source 105 including an x-ray tube. The x-ray tube may include a cathode and an anode electrically connected to a high voltage electrical circuit. Upon the energization of the electrical circuit, electrons directed from the cathode strike the anode (target) and produce high frequency electromagnetic waves, such as x-rays. Since the x-rays are generated in all directions, the x-ray tube may be enclosed in a radiation shield in order to direct the x-rays in a specific direction, such as towards a collimator. At the collimator, the beam is collimated to a desired beam size. A part of the beam may be reflected from the collimator blades may be adsorbed by a radiation shielding surrounding part of the collimator housing. The collimated beam may exit the x-ray source 105 via a dedicated port.

A filter carriage may be mounted within gantry 103 between the x-ray source 105 and the subject 104. The carriage may travel in and out of the beam in the z-direction while the beam is substantially in the y-direction. The carriage may include one or more bowtie filters and/or hardening filters. During scanning, a selected collimator and/or filter 143 may be positioned in the path of the x-ray beam 106 by adjusting a position of the carriage.

In certain embodiments, the system 100 is configured to traverse different angular positions around the subject 104 for acquiring desired projection data. Accordingly, the gantry 103 and the components mounted thereon (such as the x-ray source 105 and the detector elements 102) may be configured to rotate about a center of rotation 106 for acquiring the projection data, for example, at different energy levels. Alternatively, in embodiments where a projection angle relative to the subject 104 varies as a function of time, the mounted components may be configured to move along a general curve rather than along a segment of a circle.

In one embodiment, the system 100 includes a control mechanism 108 to control movement of the components such as rotation of the gantry 103 and the operation of the x-ray source 105. In certain embodiments, the control mechanism 108 further includes an x-ray controller 110 configured to provide power and timing signals to the x-ray source 105. Additionally, the control mechanism 108 includes a gantry motor controller 112 configured to control a rotational speed and/or position of the gantry 103 based on imaging requirements.

In certain embodiments, the control mechanism 108 further includes a data acquisition system (DAS) 114 configured to sample analog data received from the detector elements 102 and convert the analog data to digital signals for subsequent processing. The data sampled and digitized by the DAS 114 is transmitted to a computing device (also referred to as processor) 116. In one example, the computing device 116 stores the data in a storage device 118. The storage device 118, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 116 provides commands and parameters to one or more of the DAS 114, the x-ray controller 110, and the gantry motor controller 112 for controlling system operations such as data acquisition and/or processing. In certain embodiments, the computing device 116 controls system operations based on operator input. The computing device 116 receives the operator input, for example, including commands and/or scanning parameters via an operator console 120 operatively coupled to the computing device 116. The operator console 120 may include a keyboard or a touchscreen to allow the operator to specify the commands and/or scanning parameters.

Although FIG. 1 illustrates only one operator console 120, more than one operator console may be coupled to the system 100, for example, for inputting or outputting system parameters, requesting examinations, and/or viewing images. Further, in certain embodiments, the system 100 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 100 either includes, or is coupled to a picture archiving and communications system (PACS) 124. In an exemplary implementation, the PACS 124 is further coupled to a remote system such as a radiology department information system, hospital information system, and/or to an internal or external network (not shown) to allow operators at different locations to supply commands and parameters and/or gain access to the image data.

The computing device 116 uses the operator-supplied and/or system-defined commands and parameters to operate a table motor controller 126, which in turn, may control a motorized table 128. Particularly, the table motor controller 126 moves the table 228 for appropriately positioning the subject 104 in the gantry 103 for acquiring projection data corresponding to the target volume of the subject 104.

As previously noted, the DAS 114 samples and digitizes the projection data acquired by the detector elements 102. Subsequently, an image reconstructor 130 uses the sampled and digitized x-ray data to perform high-speed reconstruction. Although FIG. 1 illustrates the image reconstructor 130 as a separate entity, in certain embodiments, the image reconstructor 130 may form part of the computing device 116. Alternatively, the image reconstructor 130 may be absent from the system 100 and instead the computing device 116 may perform one or more functions of the image reconstructor 130. Moreover, the image reconstructor 130 may be located locally or remotely, and the image reconstructor 130 may be operatively connected to the system 100 using a wired or wireless network. Particularly, one exemplary embodiment may use computing resources in a "cloud" network cluster for the image reconstructor 130.

In one embodiment, the image reconstructor 130 stores the images reconstructed in the storage device 118. Alternatively, the image reconstructor 130 transmits the reconstructed images to the computing device 116 for generating useful patient information for diagnosis and evaluation. In certain embodiments, the computing device 116 transmits the reconstructed images and/or the patient information to a display 132 communicatively coupled to the computing device 116 and/or the image reconstructor 130.

FIG. 2 illustrates an example x-ray source used in the imaging system of FIG. 1. In one example, x-ray source 200 may be the x-ray source 105 in FIG. 1. The x-ray source may include an x-ray tube 202 wherein an x-ray beam is generated and a collimator 204 wherein the x-ray beam is collimated to a desired beam size.

The x-ray tube 202 may include a cathode 208 and an anode 206 (also referred herein as target) positioned opposite to one another enclosed within a vacuum vessel 205. The anode 206 may be rotated about a longitudinal axis of the pillar 215 supporting the anode 206. A high voltage electrical circuit may be electrically coupled to the x-ray tube 202 and configured to supply power to the x-ray tube 202. The power supplied to the x-ray tube 202 may create a potential difference of, for example, 60 kV to 140 kV between the cathode 208 and the anode 206, thereby causing electrons generated by the cathode 208 to accelerate towards the anode 206. As the electrons collide with the anode 206 at a high velocity, at least a portion of the kinetic energy of the electrons is converted to high frequency electromagnetic radiation, or x-rays 210.

In one example, the high voltage electrical circuit may include a cathode multiplier electrically coupled to a high voltage transformer and the cathode 208, and an anode multiplier electrically coupled to the high voltage transformer and the anode 206. The cathode multiplier may be configured to supply a negative high voltage DC to the cathode 208, for example via high voltage connection, while the anode multiplier may be configured to supply a positive high voltage DC to the anode 206, for example via high voltage connection. That is, the cathode 208 and the anode 206 may carry equal voltages of different polarity. In this way, a high voltage potential difference between the cathode 208 and the anode 206 may be generated.

The x-ray tube 202 may be enclosed in a vacuum vessel 205 including a transmissive port 244. As an example, the vessel 205 may include a first radiation shield 230 arranged to block x-rays traveling in undesirable directions. The radiation shield may enclose the entire x-ray tube except for the transmissive port 244. For example, the x-ray transmissive port 244 may comprise a circular port comprising a material through which x-rays may be transmitted without absorption. The transmissive port 244 may be positioned in the vessel 205 aligned with the point of generation of x-rays on the cathode 208. The first radiation shield 230 may be made of a heavy metal such as tungsten that is able to absorb any x-ray radiation incident on the first radiation shield 230. In one example, the first radiation shield 230 surrounding the x-ray tube 202 may be of uniform thickness. In another example, the first radiation shield 230 surrounding the x-ray tube 202 may have non-uniform thickness with certain portions thicker than others such as the corners may be thickened relative to the walls. In this way, the generated x-ray is confined within the x-ray tube and may not exit the tube except via the transmissive port 244. The cylindrical first radiation shield 230 may be lined with solid thermal insulation 240.

The radiation source may further include a collimator 204 adjoining the x-ray tube. The x-rays 210 exiting the x-ray tube 202 via the transmissive port 244 may enter the collimator. The collimator may include a first collimator blade 218 and a second collimator blade 220 positioned coaxially along a longitudinal axis A-A'. The distance between the first collimator blade 218 and the second collimator blade 220 may be adjusted to form an opening or aperture 224. The first collimator blade 218 and the second collimator blade 220 may be moved relative to each other along the A-A' axis to adjust the aperture 224 size.

The collimator 204 may be enclosed in a second radiation shield 222 except for a port 216. A portion of the x-rays 210 may pass through the opening or aperture 224 between the first collimator blade 218 and the second collimator blade 220 and the transmitted x-ray beam 214 may exit the collimator via the port 216. A portion of the x-rays impinging on the first collimator blade 218 or the second collimator blade 220 may be reflected from the respective blade and the reflected x-rays 212 may be absorbed by the second radiation shield 222. In this way, the reflected rays from the collimator blades are restricted from exiting the collimator. In one example, the second radiation shield 222 surrounding the collimator 204 may be of uniform thickness. In another example, the second radiation shield 222 surrounding the collimator 204 may have non-uniform thickness with certain portions thicker than others such as the corners may be thickened relative to the walls.

The x-ray beam 214 exiting the collimator 204 may then be directed to penetrate an object (not shown), such as human anatomical parts for medical examination and diagnostic procedures. The x-rays transmitted through the object are intercepted by a detector (not shown) and an image is formed of the internal anatomy. Further, industrial x-ray tubes may be used, for example, to inspect metal parts for cracks or to inspect the contents of luggage at airports.

The first radiation shield 230 and the second radiation shield 222 may be made of tungsten instead of lead (as being commonly used for radiation shielding). Components of the first radiation shield 230 and the second radiation shield 222 may be formed by infiltrating tungsten particles with a binder solution and then curing the binder solution impregnated with the tungsten particles.

In one example, the tungsten particles may be filled in cavity of a mold, the cavity shaped according to a shape of the radiation shielding component. The binder solution is added to the cavity under vacuum after filling the cavity with tungsten particles. The curing may include placing the mold with the tungsten particles and binder solution in an oven at a temperature below 200° C. After curing, the radiation shielding component may be separated from the mold by dissolving a releasing layer between the mold and the component in a solvent.

In another example, alternate layers of tungsten powder and the binding agent may be deposited on a 3D binder jetting printer based on a selected geometry of the component. The binding agent is deposited on a bed of tungsten powder via one or more inkjet nozzles following the selected geometry of the component. The component may then be immersed in a solution of the binding agent to infiltrate the component with the binding agent, the binding agent entering porous parts of the component via capillary action. After infiltrating with the binding agent and prior to curing the component, excess binding agent adhering to a surface of the component may be removed.

The radiation shielding component may include a plurality of interdigitated parts with copper infiltrated across junctions between digits of adjacent parts. Each part of the plurality of interdigitated parts may be a panel manufactured with tungsten by a binder jetting process. The panel may include a plurality of digits and a plurality of indentations on at least two, opposite sides. Two consecutive digits of the plurality of digits may be separated by an indentation. The thickness of the panel is lower than 20% of a width and/or a length of the panel. The panel may be coupled to another panel by coupling a plurality of digits on a side of the panel with a plurality of indentations on a side of the another panel. The copper may be infiltrated via capillary action by positioning the panel coupled to another panel in contact with copper beads or powder inside a vacuum furnace, the copper filling gaps between the plurality of digits coupled to the plurality of indentations.

FIG. 5 shows an example method 500 for manufacturing a radiation shielding component via a binder reactive injection molding process. The radiation shielding component may be used in the first radiation shield 230 and/or the second radiation shield 222 as shown in FIG. 2.

At 502, a mold is prepared for the component (also referred herein as part) to be manufactured. The mold may be prepared via one or more of machining, additive printing, traditional casting, and injection molding. The materials used in the mold may be any polymer that is chemically and thermal compatible with the material and process of reactive injection molding. Since the binder reactive injection molding process is carried out at a lower temperature (such as not exceeding 200° C.), the polymer or metals used for the mold may not need a high thermal compatibility. As examples cost effective polymers used in the mold may be epoxies, silicones, Ultem, Kapton, polyether ether ketone (PEEK), etc. As examples cost effective metals such as aluminum, steel, copper, etc. may be used in the mold. The mold can be made with a single material or a combination of materials. The mold may be coated with a releasing/sacrificing layer. The releasing or sacrificing layer may be coated using any coating methods known in the art, such as thin film coating processes or additive printing. Further, the releasing or sacrificing layer may be composed of mold-releasing spray chemicals or polymers which may be peeled off or dissolved by organic or aqueous solvents to facilitate demolding.

Figure 3A:
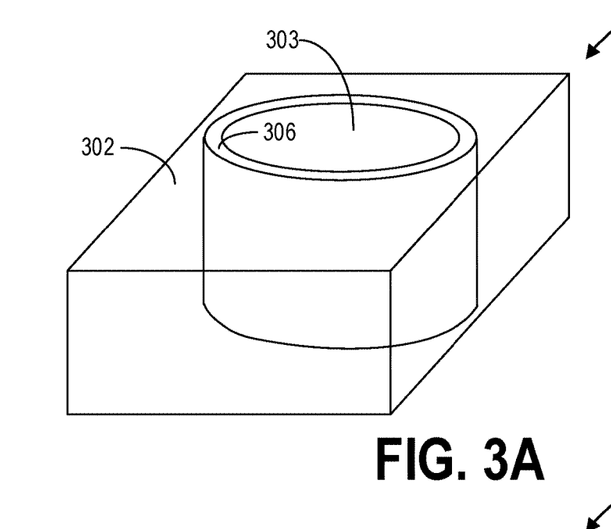
FIG. 3A shows a first step in a binder reactive injection molding process for manufacturing a radiation shielding component.

FIG. 3A shows a first step 300 in a binder reactive injection molding process for manufacturing a radiation shielding component. A mold 302 is prepared and conditioned for the injection molding process. In this example, a cylindrical mold 302 is being used with a hollow ring (cavity) 306 enclosing a solid portion 303. The inner walls of the cavity 306 may be coated with the aforementioned releasing agent to facilitate in the demolding process. Numerous configurations may be hollowed out within the mold 302 depending on a desired shape of the shielding component that is manufactured. In this example, a cylindrical cavity is depicted, though it will be appreciated that numerous other mold configurations may be employed within the scope of the present disclosure.

Returning to FIG. 5, at 504, the cavity of the mold may be filled with metal particles such as metal micro particles or nanoparticles. In one example, the cavity of the mold may be filled with Tungsten particles. The metal particle size may range from 0.1 to 300 micrometers in diameter. The size of the metal particles used may be varied based on part design and application requirements such as shielding efficiency, surface roughness, etc. In one example, for a component of a radiation shield in an x-ray tube, metal particles of average diameter of 10-50 micrometers may be used. The cavity of the mold may be filled 95% by volume with the metal particles. The metal particles may be filled in the cavity of the mold with or without application of pressure. By applying pressure, the close packing of metal particles within the cavity may be improved. Each metal particle in the cavity may be in face sharing contact with one or more proximal metal particles to form a close packing.

The amount of tungsten loading can be controlled either by the particle size or by adding other metal or inorganic particles to adjust the tungsten loading. For example, adding copper particles can further increase thermal conductivity of the shielding parts. The mechanical strength of the parts may be further adjusted with particle loading with additives such as mechanical strengtheners, inorganic/organic fibers, etc.

Figure 3B:
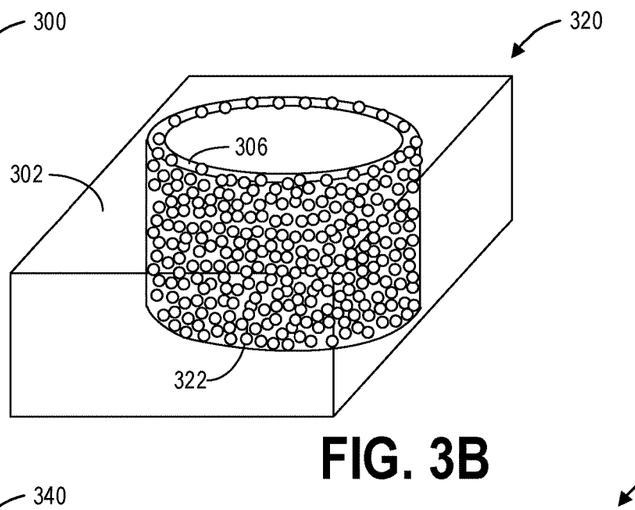
FIG. 3B shows a second step in the binder reactive injection molding process for manufacturing the radiation shielding component.

FIG. 3B shows a second step 320 in a binder reactive injection molding process for manufacturing a radiation shielding component. The cavity 306 of the mold may be filled with metal particles 322. During filling the cavity 306 of the mold 302 with metal particles, the mold may be placed in a pressurized chamber with a pressure of 0-100 pounds per square inch (psi)applied on the mold.

Returning to FIG. 5, at 506, the metal particles packed in the cavity of the mold may be infiltrated with a binder solution. The binder solution includes organic or inorganic binder. The binders may be thermosetting or thermoplastic polymer precursors that can be polymerized/crosslinked to form solid polymer matrix. The initial viscosities of the binder solutions may range from 10-100,000 cps (centipoise). In one example, binder solutions with viscosities in the range of 50-15,000 cps may be used in this process. The organic binders may be any polymers that have strength to hold the metal particles and survive the service lifetime for the parts. Example polymers used as binders include epoxies, polyurethanes, phenol-formaldehyde, melamine resin, polyacrylates, polyimides, etc. Examples of inorganic binders include gypsum, lime, cements, etc. As the binder solution is added to the cavity (filled with metal particles), the binder solution may infiltrate the space remaining amongst the metal particles. The binder solution may occupy 5% by volume of the mold cavity. The binder solution may be added without or without vacuum.

Figure 3C:
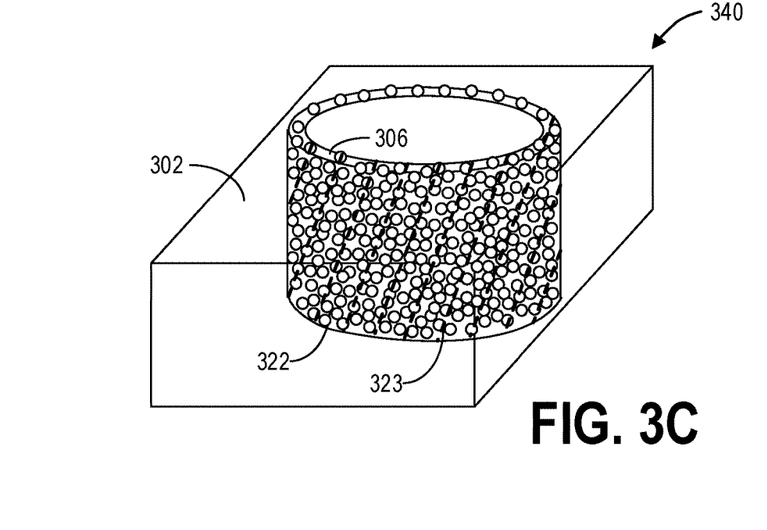
FIG. 3C shows a third step in the binder reactive injection molding process for manufacturing the radiation shielding component.

FIG. 3C shows a third step 340 in a binder reactive injection molding process for manufacturing a radiation shielding component. The cavity 306 of the mold may be completely filled with metal particles 322 and a binder solution 323. Together the metal particles and the binder solution may completely occupy the entire volume of the cavity 306. During filling the cavity 306 of the mold 302 with the binder solution, the mold may be placed in a chamber with lower pressure (vacuum). By applying vacuum during addition of binder solution to the mold, retention of air in the binder solution may be reduced. In this way, undesired air pockets may be reduced in the final cured component.

Returning to FIG. 5, at 508, the binder solution impregnated with metal particles inside the cavity of the mold may be cured. Curing is a process wherein the binder solution polymerizes/crosslinks to form a polymer-metal solid composite. The shape of the final solid composite is that of the cavity of the mold in which the mixture is cured. The strength of the polymer is increased due to the polymerization/cross linking and the metal particles provide reinforcement to the polymer matrix. Due to the high concentration (such as 95% by volume) of tungsten metal particles, the cured part may be used for radiation shielding. The curing polymerization reaction may be conducted at room temperature or at slightly elevated temperatures (e.g., less than 200° C.). As an example, the curing may be carried out in the temperature range of 15° C. (room temperature)-200° C. The mold with the metal particles impregnated with the binder solution may be placed in an oven at the elevated temperature to cure the metal particles-binder solution mixture and form a cross-linked metal-polymer composite.

Figure 3D:
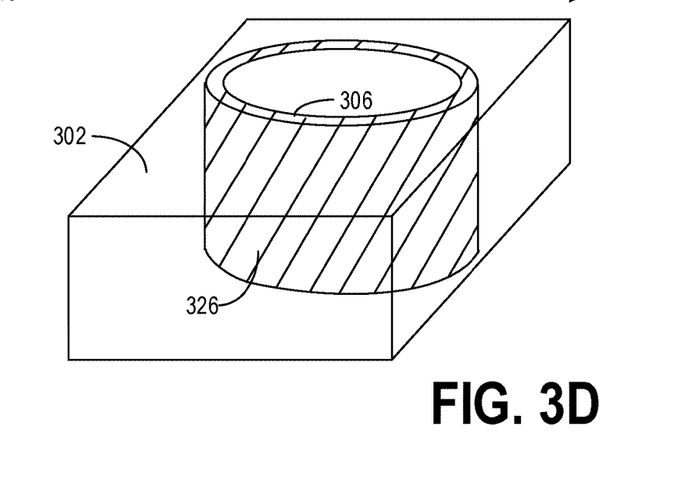
FIG. 3D shows a fourth step in the binder reactive injection molding process for manufacturing the radiation shielding component.

FIG. 3D shows a fourth step 360 in a binder reactive injection molding process for manufacturing a radiation shielding component. In this step, the metal particles-binder solution mixture is cured to form a solid polymer-metal composite. The shape of the composite structure may be that of the cavity 306 of the mold. Due to the high concentration of metal particles in the composite, the final part may exhibit physical properties of that of the metal. Due to the high metal particle concentration, the particles may be connected (in physical contact) to offer desired radiation shielding and thermal conductivity. In this example, as tungsten particles are used in the composite, the final part displays the radiation shielding properties of tungsten.

Returning to FIG. 5, at 510, the composite part may be demolded. Demolding includes removing the cured, solid part from inside the cavity of the mold. The releasing layer applied to the inner walls of the cavity may be physically separated or dissolved by solvents/water to facilitate the demolding process.

In this way, a component of the radiation shield used in an imaging system may be manufactured without use of high temperature or complicated machining. A much wider choice of binder solutions may be used in a binder reactive injection molding process relative to the binder solution options available for printing commercial parts. This process offers faster manufacture speed, lower cost compared to traditional machining and/or casting/molding heavy metal parts by eliminating expensive tooling, furnace usage, and high energy consumption.

FIG. 6 shows an example method 600 for manufacturing a radiation shielding component via a binder jetting and infiltration process. The radiation shielding component may be used in the first radiation shield 230 and/or the second radiation shield 222 as shown in FIG. 2. The binder reactive injection molding process for manufacturing radiation shielding components may be used to make simpler geometries which can be formed (such as machined) in a mold. Whereas the binder jetting and infiltration process allows manufacture of components with more complicated geometries (such as parts that are undercut or with embedded hollow structures) which may be directly used in a radiation shield. By manufacturing the component as a single part instead of multiple pieces, assembly may be avoided and reduction in the usage of holes, joints, and connections improved radiation shielding of the component.

At 602, the component (also referred herein as a part) may be printed using a 3D binder jetting or lithography based printer. In a binder jetting process, a binder is selectively deposited onto a powder bed, bonding the areas containing the powder together to form a solid part one layer at a time. A blade may spread a thin layer of metal (such as Tungsten) powder over a build platform. The layout of the powder on the build platform may be based on the geometry of the final component. The metal powder size may range from 0.1 to 300 micrometers in diameter. The size of the metal powder particles used may be varied based on part design and application requirements such as shielding efficiency, surface roughness, etc. In one example, for a component of a radiation shield in an x-ray tube, metal particles of average diameter of 10-50 micrometers may be used.

Then a carriage with inkjet nozzles is passed over the bed, selectively depositing a binding agent that bonds the deposited particles together. The deposition of the binding agent may also be based on the geometry of the final component. When deposition of binding agent is completed and the layer has solidified, the build platform may be moved downward and the blade re-coats the surface of the solidified metal composite layer. The binding agent is again deposited on the newly coated layer and the process is repeated until the entire component has been printed. The binding agent may include organic or inorganic binders. The binders may be thermosetting or thermoplastic polymer precursors that can be polymerized/crosslinked to form solid polymer matrix. Most binders used in binder jetting may be mixed with water/solvents or a mixture of water and solvents to enable a lower viscosity for smooth and stable jetting. Examples of binders are polyacrylates, poly(vinyl alcohol), carbohydrates such as polysaccharides or mono- or di-saccharides, hydrolyzed starches, etc.

This printing method provides flexibility in component design. As an example, the thickness of the parts at different locations of the shield may be varied such as the corners of a shield may be made thicker relative to the walls. In this way, the need to manufacture unnecessarily thick and heavy parts may be eliminated.

Figure 4A:
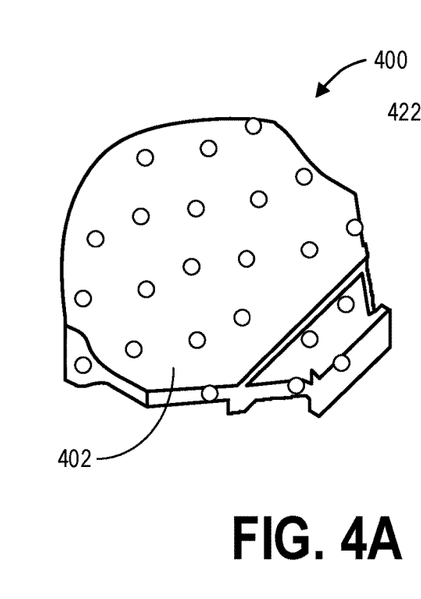
FIG. 4A shows a first step in a binder jetting and infiltration process for manufacturing a radiation shielding component.

FIG. 4A shows a first step 400 in a binder jetting and infiltration process for manufacturing a radiation shielding component. In this step, as described above, the component 402 of a desired geometry may be printed using a 3D binder jet printing process. However, due to use of lower viscosity binding agents, a component printed via the binder jetting process may be porous and may lack bonding strength to be directly used in the radiation shield.

Returning to FIG. 6, at 604, the part may be immersed in a binging agent solution. In this post-infiltration process, the polymeric binders may infiltrate the porous part via capillary action, and upon curing, may add strength to the part and enable the part to be used directly for radiation shielding applications. The post-infiltration process may be carried out at room temperature and due to the lower temperature operation, the possibility that the part may break or crack due to the thermal mismatching may be reduced. The initial viscosities of the binder solutions may range from 10-100,000 cps. In one example, binder solutions with viscosities in the range of 50-15,000 cps may be used in this process. The organic binders may be any polymers that have strength to hold the metal particles and survive the service lifetime for the parts. Example polymers used as binders include epoxies, polyurethanes, phenol-formaldehyde, melamine resin, polyacrylates, polyimides, etc. Examples of inorganic binders include gypsum, lime, cements, etc.

One example approach to infiltrate the part with binder solution includes spray coating the parts until reaching a specified binder loading ratio. Another example approach may include inserting the part in a vacuum chamber which has multiple inlets and outlets to allow both applying vacuum and fill binder solutions. The chamber may be first evacuated and then filled with binder solution to fill the voids inside the part. The infiltration volume of the binder may be controlled by a volume meter.

Figure 4B:
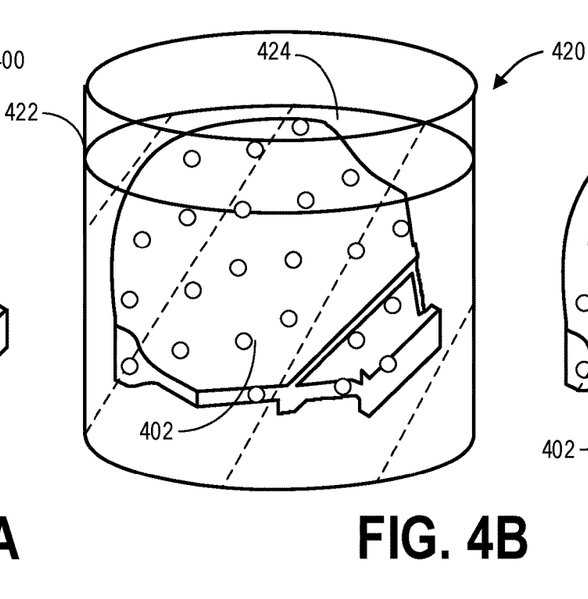
FIG. 4B shows a second step in the binder jetting and infiltration process for manufacturing the radiation shielding component.

FIG. 4B shows a second step 420 in the binder jetting and infiltration process for manufacturing the radiation shielding component. In this step, the part 402 as manufactured by the binder jetting process is submerged in a binder solution 424. In this example, the part 402 in placed in a container 422 along with the binder solution 424. The part 402 may be first placed in the container 422 and then the binder solution 424 may be added or the part 402 may be inserted into the container 422 containing the binder solution 424. During filling the container 422 with the binder solution 424, the container 422 may be placed in a chamber with lower pressure (vacuum). By applying vacuum during addition of binder solution to the container 422, retention of air in the binder solution in contact with the part 402 may be reduced. In this way, undesired air pockets may be reduced in the final cured component.

Returning to FIG. 6, at 606, after a predetermined duration of time, the part may be removed from the binder solution and excess binder solution may be removed from the part. The excess resin on the exposed surface area of the part may be removed by wiping or blow drying.

Figure 4C:
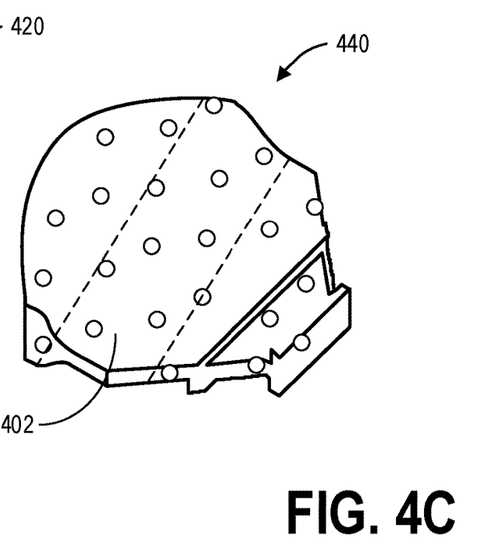
FIG. 4C shows a third step in the binder jetting and infiltration process for manufacturing the radiation shielding component.

FIG. 4C shows a third step 440 in the binder jetting and infiltration process for manufacturing the radiation shielding component. In this step, the part 402 may be wiped or blow dried to remove any excess binder solution adhering to the surface of the part. By removing the excess binder from the part, the surface roughness of the part (upon curing) may be reduced and the finishing of the part may be improved.

Returning to FIG. 6, at 608, the part infiltrated with binder solution may be cured. Curing is a process wherein the binder solution polymerizes/crosslinks to form a polymer-metal solid composite. The strength of the polymer is increased due to the polymerization/cross linking and the metal particles provide reinforcement to the polymer matrix. Therefore, by infiltrating the porous part manufactured via binder jetting and then curing the part, strength of the part may be increased. Due to the high concentration of tungsten metal particles, the cured part may be used for radiation shielding. The curing polymerization reaction may be conducted at room temperature or at slightly elevated temperatures (e.g., less than 200° C.) inside an oven. As an example, the curing may be carried out in the temperature range of 15° C. (room temperature)-200° C. In one example, vacuum may be applied during curing to remove any trapped air particles in the part.

Figure 4D:
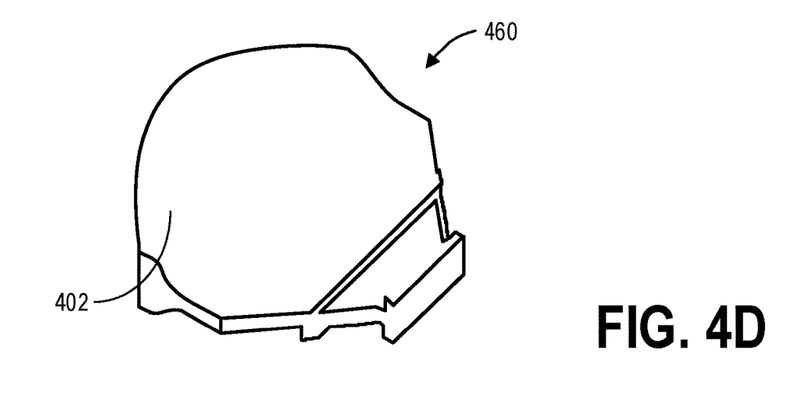
FIG. 4D shows a fourth step in the binder jetting and infiltration process for manufacturing the radiation shielding component.

FIG. 4D shows a fourth step 460 in the binder jetting and infiltration process for manufacturing a radiation shielding component. In this step, the part 402 infiltrated with binder solution is cured to form a solid polymer-metal composite part. Due to the high concentration of metal particles in the composite, the final part may exhibit physical properties of that of the metal. In this example, as tungsten particles are used in the composite, the final part displays the radiation shielding properties of tungsten. Due to the ability to fabricate complex geometries using the binder jetting process and the subsequent strengthening of the part by infiltration and curing, a part manufactured by this process may be directly utilized in the radiation shield of an x-ray apparatus.

In one example, by using a stronger binder during directly printing tungsten powder through binder jetting, the part may be used as-printed (without the need for post printing infiltration). In another example, the metal powder may be mixed with binder powder and then high precision laser sintering of the polymer with the metal powder may be carried out and a part manufactured by this process may also be used as-printed.

In one example, a manufacturing method, comprises: forming a radiation shielding component including: printing the component with metal powder, infiltrating the component with a binding agent, and curing the component to polymerize the binding agent. In the preceding example, additionally or optionally, the printing includes a 3-dimensional binder jetting printing comprising: depositing alternate layers of the metal powder and the binding agent based on a selected geometry of the component. In any or all of the preceding examples, additionally or optionally, the metal powder is tungsten powder. In any or all of the preceding examples, additionally or optionally, the binding agent is a thermosetting polymer precursor or a thermoplastic polymer precursor. In any or all of the preceding examples, additionally or optionally, the binding agent is deposited on a bed of the metal powder via one or more inkjet nozzles following the selected geometry of the component. In any or all of the preceding examples, additionally or optionally, the infiltrating includes immersing the component in a solution of the binding agent, the binding agent entering porous parts of the component via capillary action. In any or all of the preceding examples, additionally or optionally, the immersing is carried out in vacuum. In any or all of the preceding examples, additionally or optionally, the infiltrating further includes spray coating the component with the binding agent. In any or all of the preceding examples, the method further comprising, additionally or optionally, removing excess binding agent adhering to a surface of the component. In any or all of the preceding examples, additionally or optionally, the curing the component includes forming a polymer-metal composite by exposing the component to a curing temperature in a range of 65-200° C. In any or all of the preceding examples, additionally or optionally, the radiation shielding component includes panels with digits along one or more sides, the radiation shielding component enclosing an x-ray tube or an x-ray collimator.

Another example method comprises: forming a radiation shielding component by infiltrating tungsten particles with a binder solution and then curing the binder solution impregnated with the tungsten particles. In the preceding example, additionally or optionally, the tungsten particles are filled in cavity of a mold, the cavity shaped according to a shape of the radiation shielding component. In any or all of the preceding examples, additionally or optionally, the cavity is filled with tungsten particles under atmospheric or a higher than atmospheric pressure. In any or all of the preceding examples, additionally or optionally, the binder solution is added to the cavity under vacuum after filling the cavity with tungsten particles. In any or all of the preceding examples, additionally or optionally, the curing includes placing the mold with the tungsten particles and the binder solution in an oven at a temperature below 200° C. In any or all of the preceding examples, the method further comprising, additionally or optionally, separating the radiation shielding component from the mold by dissolving a releasing layer between the mold and the component in a solvent.

In yet another example, a method, comprises: forming a radiation shielding component including a tungsten-polymer composite, the tungsten-polymer composite comprising tungsten particles dispersed in a polymer matrix. In the preceding example, additionally or optionally, the tungsten-polymer composite is formed by depositing alternate layers of the tungsten particles and a polymer precursor, infiltrating the tungsten particles with the polymer precursor, and then curing the polymer precursor infiltrated with the tungsten particles. In any or all of the preceding examples, additionally or optionally, the tungsten-polymer composite is further formed by filling the tungsten particles in a cavity of a mold, infiltrating the tungsten particles in the cavity with the polymer precursor, and then curing the polymer precursor infiltrated with the tungsten particles.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A manufacturing method, comprising: forming a radiation shielding component including: printing the component with metal powder; wherein the metal powder is tungsten powder; infiltrating the component with a binding agent, the infiltrating including immersing the component in a solution of the binding agent, the binding agent entering porous parts of the component via capillary action, wherein the immersing is carried out in a vacuum; and curing the component to polymerize the binding agent.

2. The method of claim 1, wherein the printing includes a 3-dimensional binder jetting printing comprising: depositing alternate layers of the metal powder and the binding agent based on a selected geometry of the component.

3. The method of claim 2, wherein the binding agent is a thermosetting polymer precursor or a thermoplastic polymer precursor.

4. The method of claim 2, wherein the binding agent is deposited on a bed of the metal powder via one or more inkjet nozzles following the selected geometry of the component.

5. The method of claim 1, further comprising removing excess binding agent adhering to a surface of the component.

6. The method of claim 1, wherein the curing the component includes forming a polymer-metal composite by exposing the component to a curing temperature in a range of 15° C.-200° C.

7. The method of claim 1, wherein the radiation shielding component, once formed, includes panels with digits along one or more sides, the radiation shielding component configured to enclose an x-ray tube or an x-ray collimator.

8. A method, comprising:
forming a radiation shielding component by infiltrating tungsten particles with a binder solution and then curing the binder solution impregnated with the tungsten particles, wherein the tungsten particles are filled in cavity of a mold, the cavity shaped according to a shape of the radiation shielding component; and
separating the radiation shielding component from the mold by dissolving a releasing layer between the mold and the component in a solvent.

9. The method of claim 8, wherein the cavity is filled with tungsten particles under an atmospheric pressure or a higher than atmospheric pressure.

10. The method of claim 8, wherein the binder solution is added to the cavity under vacuum after filling the cavity with tungsten particles.

11. The method of claim 8, wherein the curing includes placing the mold with the tungsten particles and the binder solution in an oven at a temperature below 200° C.

12. A method, comprising:
forming, via an infiltration casting method that includes infiltrating a polymer precursor, a radiation shielding component including a tungsten-polymer composite, the tungsten-polymer composite comprising tungsten particles dispersed in a polymer matrix, the radiation shielding component comprising 95% by volume tungsten.

13. The method of claim 12, wherein the infiltration casting method includes depositing alternate layers of the tungsten particles and the polymer precursor, infiltrating the tungsten particles with the polymer precursor, and then curing the polymer precursor infiltrated with the tungsten particles to thereby form the polymer matrix with the tungsten particles dispersed therein.

14. The method of claim 12, wherein the infiltration casting method includes filling the tungsten particles in a cavity of a mold, infiltrating the tungsten particles in the cavity with the polymer precursor, and then curing the polymer precursor infiltrated with the tungsten particles to thereby form the polymer matrix with the tungsten particles dispersed therein.

* * * * *